United States Patent
Ogawa et al.

(10) Patent No.: US 10,914,726 B2
(45) Date of Patent: Feb. 9, 2021

(54) METHOD FOR EVALUATING PROTRUSION-FORMING ABILITY OF CELL SPHEROIDS

(71) Applicant: OLYMPUS CORPORATION, Hachioji (JP)

(72) Inventors: Mayu Ogawa, Tokyo (JP); Kazuhito Goda, Tokyo (JP); Kosuke Takagi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 217 days.

(21) Appl. No.: 16/181,782

(22) Filed: Nov. 6, 2018

(65) Prior Publication Data

US 2019/0145959 A1    May 16, 2019

(30) Foreign Application Priority Data

Nov. 10, 2017   (JP) .................................. 2017-217805

(51) Int. Cl.
| | |
|---|---|
| *G06K 9/00* | (2006.01) |
| *G01N 33/50* | (2006.01) |
| *G01N 21/64* | (2006.01) |
| *G01N 21/17* | (2006.01) |

(52) U.S. Cl.
CPC ..... *G01N 33/5011* (2013.01); *G01N 21/6428* (2013.01); *G01N 21/6458* (2013.01); *G01N 2021/1787* (2013.01); *G01N 2021/6439* (2013.01)

(58) Field of Classification Search
None
See application file for complete search history.

(56) References Cited

U.S. PATENT DOCUMENTS

| | | | |
|---|---|---|---|
| 2012/0302572 A1 | 11/2012 | Kan et al. | |
| 2014/0221225 A1* | 8/2014 | Danen ............... | G01N 33/5005 506/9 |
| 2016/0011168 A1 | 1/2016 | Iwamoto et al. | |

FOREIGN PATENT DOCUMENTS

| | | |
|---|---|---|
| JP | 2016017835 A | 2/2016 |
| JP | 2017113000 A | 6/2017 |

OTHER PUBLICATIONS

Eric B. Berens, et al., "A Cancer Cell Spheroid Assay to Assess Invasion in a 3D Setting," Journal of Visualized Experiments, Nov. 2015, 105, e53409, 6 Pages.

* cited by examiner

*Primary Examiner* — Atiba O Fitzpatrick
(74) *Attorney, Agent, or Firm* — Holtz, Holtz & Volek PC

(57) ABSTRACT

The present invention provides a method for evaluating a protrusion-forming ability of cell spheroids, comprising step (a) of imaging a cell spheroid labeled with a fluorescent substance using a fluorescence microscope at a resolution capable of identifying individual cells, and acquiring a plane tomographic image of a fluorescence emitted from the fluorescent substance, step (b) of analyzing the plane tomographic image acquired in step (a) to determine a protrusion part of the cell spheroid, and step (c) of evaluating a protrusion-forming ability of the cell spheroid based on the protrusion part determined in step (b).

11 Claims, 2 Drawing Sheets

METHOD FOR EVALUATING PROTRUSION-FORMING ABILITY OF CELL SPHEROIDS

BACKGROUND OF THE INVENTION

Field of the Invention

The present invention relates to a method for evaluating a protrusion-forming ability of cell spheroids by image analysis of the shape of the cell spheroids.

Priority is claimed on Japanese Patent Application No. 2017-217805, filed Nov. 10, 2017, the content of which is incorporated herein by reference.

Description of Related Art

In recent years, a cell invasion assay has been widely used to evaluate the cell migration/invasion ability. As this cell invasion assay, systems for evaluating the invasion of plane-cultured (monolayer cultured) cells are a mainstream. As examples of the invasion assay of plane-cultured cells, a method may be mentioned in which a Boyden chamber is used which is partitioned into an upper layer and a lower layer by a membrane capable of being permeated by only cells having migration/invasion ability, for example, a polycarbonate membrane; and cells are seeded on the upper layer and cultured for a predetermined period of time, followed by detecting the cells transferred to the lower layer by a colorimetric method or the like. In addition, a method may also be mentioned in which cells are seeded on only a part of the bottom surface of the cell container and cultured for a predetermined time, and then the cells present in the part where cells have not been seeded at the start of the culture are detected. However, in these cell invasion assays, it is impossible to evaluate the migration/invasion ability in a state where the cells form a three-dimensional structure, such as in vivo.

On the other hand, in recent research, it has been reported that Epithelial Mesenchymal Transition (EMT) plays a critical role in the malignant progression of cancer and is involved in cancer metastasis (for example, Patent Document 1: Japanese Unexamined Patent Application Publication No. 2016-17835; Patent Document 2: Japanese Unexamined Patent Application Publication No. 2017-113000). EMT is a process in which epithelial cells lose their cell polarity and cell adhesion ability to acquire invasion and migration properties, thereby changing into the mesenchymal-like cells. For this reason, evaluating the migration/invasion ability of the cells in a state of being treated with anticancer agents is important for the evaluation of sensitivity to anticancer agents. When evaluating anticancer agents, it is desirable to evaluate the acting effect in a microenvironment caused by a three-dimensional structure of the cancer tissue. However, in the conventional cell invasion assay using plane-cultured cells, it is impossible to reproduce the microenvironment of cancer tissues. Therefore, a method for evaluating migration/invasion ability of cancer cells with a three-dimensional structure imitating the microenvironment of cancer tissues in vivo is desired.

Several methods for evaluating the migration/invasion ability of cells using three-dimensional structures of cells have been reported. For example, Non-patent Document 1 (Berens et al., Journal of Visualized Experiments, 2015, Nov. 20; (105). doi:10.3791/53409) discloses a method in which cell spheroids of cancer cells embedded in a gel were cultured to form a protrusion structure; and then the cell spheroids were imaged using a transmission light microscope from the upper side; followed by evaluating the migration/invasion ability based on the area value of the formed protrusion structure region in the obtained transmitted light plane image.

SUMMARY OF THE INVENTION

An object of the present invention is to provide a method for evaluating a protrusion-forming ability of cell spheroids, in which cell spheroids of three-dimensional structure are used, and the shape thereof is imaged and analyzed so as to evaluate the protrusion-forming ability thereof.

The present invention provides the following methods for evaluating a protrusion-forming ability of cell spheroids.

[1] A method for evaluating a protrusion-forming ability of cell spheroids, comprising
    step (a) of imaging a cell spheroid labeled with a fluorescent substance using a fluorescence microscope at a resolution capable of identifying individual cells, and acquiring a plane tomographic image of a fluorescence emitted from the fluorescent substance,
    step (b) of analyzing the plane tomographic image acquired in step (a) to determine a protrusion part of the cell spheroid, and
    step (c) of evaluating a protrusion-forming ability of the cell spheroid based on the protrusion part determined in step (b).

[2] The method according to [1], wherein
    in step (a), two or more plane tomographic images of the fluorescence emitted from the fluorescent substance are acquired, the tomographic images having different focal positions, and
    in step (b), the two or more plane tomographic images acquired in step (a) are superimposed to construct a stereoscopic image of the cell spheroid, and the stereoscopic image is analyzed to determine the protrusion part of the cell spheroid.

[3] The method according to [1] or [2], wherein
    the cell spheroid to be imaged in step (a) is a cell spheroid in which a cytoskeleton is further fluorescently labeled.

[4] The method according to any one of [1] to [3], wherein
    the cell spheroid to be imaged in step (a) is a cell spheroid in which the nucleic acid is further fluorescently labeled, and in step (a), a plane tomographic image of the fluorescence emitted from the nucleic acid is also acquired.

[5] The method according to [4], wherein
    the method further comprises step (d) of analyzing the plane tomographic image of the fluorescence emitted from the nucleic acid of the cell spheroid to determine live/dead of the respective cells constituting the cell spheroid.

[6] The method according to any one of [1] to [5], wherein
    in step (c), the protrusion-forming ability of the cell spheroid is evaluated based on a length, maximum width, or presence/absence of branching of the each protrusion formed on the cell spheroid.

[7] The method according to any one of [1] to [5], wherein
    in step (c), the protrusion-forming ability of the cell spheroid is evaluated based on one or more selected from the group consisting of a number, directionality, maximum length, average length per protrusion and average number of branches per protrusion of the protrusions formed on the cell spheroid.

[8] The method according to any one of [1] to [5], wherein
    in step (c), the protrusion-forming ability of the cell spheroid is evaluated based on a ratio between a total volume of the cell spheroid and a volume of a substantially spherical central part of the cell spheroid.

[9] The method according to any one of [1] to [5], wherein in step (c), the protrusion-forming ability of the cell spheroid is evaluated based on a ratio between a volume of the protrusion and a volume of a substantially spherical central part of the cell spheroid.

[10] The method according to any one of [1] to [5], wherein in step (c), the protrusion-forming ability of the cell spheroid is evaluated based on a ratio between a volume of the protrusion and a total volume of the cell spheroid.

[11] The method according to any one of [1] to [10], wherein the cell spheroid is embedded in a gel.

[12] The method according to claim 11, wherein the cell spheroid in which the protrusion is labeled with the fluorescent substance in step (a) is obtained by applying an external stimulation to the cell spheroid embedded in the gel to form a protrusion, and then labelling the protrusion with the fluorescent substance, and the protrusion-forming ability is evaluated in a state where the cell spheroid is applied with the external stimulation.

[13] The method according to [12], wherein the external stimulation is a physiologically active substance, and the cell spheroid to be imaged in step (a) is a cell spheroid in which a protrusion is formed on the cell spheroid after contacting with a physiologically active substance, and labeled with a fluorescent substance.

[14] The method according to [13], wherein the physiologically active substance is an anticancer agent.

[15] The method according to [12], wherein the external stimulation is a non-ionizing radiation or ionizing radiation, and the cell spheroid to be imaged in step (a) is a cell spheroid in which the protrusion is formed on the cell spheroid after irradiating at least a part of the cell spheroid embedded in the gel with the non-ionizing radiation or ionizing radiation, and labeled with the fluorescent substance.

In the method for evaluating a protrusion-forming ability of cell spheroids according to the present invention, a fluorescence labeling is performed on the cell spheroids, a fluorescent image is captured at a resolution capable of identifying individual cells, and the obtained fluorescent image is image-analyzed to determine the protrusions. Therefore, according to the method for evaluating a protrusion-forming ability of cell spheroids of the present invention, it is possible to evaluate the protrusion-forming ability of the cells in a state of forming a three-dimensional structure quantitatively and more easily than the genetic analysis etc.

DETAILED DESCRIPTION OF THE INVENTION

Figure 1:
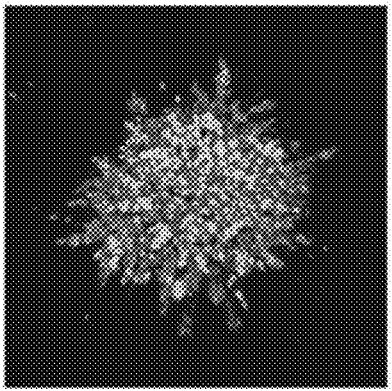
FIG. 1 shows the binarized images of the anticancer agent-untreated sample and the Batimastat-treated sample in Example 1, the samples being treated with the live/dead determination reagent.

The method for evaluating a protrusion-forming ability of cell spheroids according to the present invention (hereinafter may be referred to as "protrusion-forming ability evaluation method according to the present invention") is a method for evaluating a protrusion-forming ability of cell spheroids, including the following steps (a) to (c):

step (a) of imaging a cell spheroid labeled with a fluorescent substance using a fluorescence microscope at a resolution capable of identifying individual cells, and acquiring a plane tomographic image of a fluorescence emitted from the fluorescent substance, step (b) of analyzing the plane tomographic image acquired in step (a) to determine a protrusion part of the cell spheroid, and step (c) of evaluating a protrusion-forming ability of the cell spheroid based on the protrusion part determined in step (b).

The cell spheroid to be evaluated for the protrusion-forming ability in the present invention is not particularly limited as long as it is constituted of adherent cells capable of constructing a cell spheroid. The adherent cells constructing the cell spheroid may be, for example, cells collected from animals, primary cultured cells, further subcultured cells, cells obtained by subjecting the cells collected from animals or cells obtained by culturing thereof to various treatments, or cultured cell strains. The species from which the adherent cells constructing the cell spheroid is derived is not particularly limited as long as it is an animal, and may be, for example, a human or a non-human animal. As the non-human animal, primates such as monkeys, laboratory animals such as mice, rats, guinea pigs, rabbits, pigs, cattle, horses, sheep, dogs, cats, livestock or pets are preferable.

As the adherent cells constructing the cell spheroid, they may be cells having a pluripotency such as embryonic stem cells (ES cells), induced pluripotent stem cells (iPS cells), mesenchymal stem cells (MSC) and the like, or cells obtained by differentiating and inducing from the cells having pluripotency. Also, they may be germ cells or mature somatic cells after differentiation such as epithelial cells, hepatocytes, muscle cells or the like.

The adherent cells constructing the cell spheroid may be normal cells or cells in which abnormality has occurred in any of physiological functions, such as cancer cells, or may be both of cells in which abnormality has occurred in any of physiological functions and normal cells. Cancer cells in which EMT has occurred are highly invasive and can form protrusions, especially even in the state of being embedded in gels. Therefore, for example, by carrying out the protrusion-forming ability evaluation method according to the present invention to evaluate the protrusion-forming ability of the cancer cells, the presence/absence of EMT of cancer cells can also be evaluated.

In the present invention, the cell spheroid to be evaluated for protrusion-forming ability may be constructed from only one type of cells or may be constructed from two or more types of cells. When constructed from two or more types of cells, it may be a cell spheroid constructed only from the cells derived from the same species, or a cell spheroid constructed from the cells derived from two or more species.

In the present invention, the cell spheroid to be evaluated for protrusion-forming ability may be constructed by a conventional method. Specifically, a method in which, for example, a cell suspension containing a predetermined number of cells is injected into a U-bottom culture vessel having a low cell-adhesion property on the inner wall surface, and the cell suspension is allowed to stand for a predetermined time to form a cell spheroid, may be used. As the U-bottom culture vessel, a commercially available container for cell culture generally used for spheroid formation, a well plate in which the bottom surface and the inner wall surface thereof are coated with a low cell-adhesion substance, or the like may be used.

In the present invention, it is preferable that the cell spheroid to be evaluated for protrusion-forming ability be previously embedded in a gel before forming the protrusion. By embedding in a gel, it is possible to more clearly determine the protrusion newly formed from the original cell spheroid.

As the gel used to embed the cell spheroid, a gel constructed by one or more components constituting extracellular matrix is preferable. By embedding the cell spheroid with a gel composed of an extracellular matrix, it is possible to simulate the cellular environment in vivo, and evaluate the protrusion-forming ability under an environment closer to in vivo. Examples of the components constituting the extracellular matrix include collagen, elastin, fibronectin, laminin, entactin, heparin sulfate and the like. In particular, when evaluating the protrusion-forming ability of the cell spheroid constituted of the cells whose invasion ability to the extracellular matrix greatly affects the protrusion-forming ability, it is preferable to embed the cell spheroid in a gel composed of an extracellular matrix prior to protrusion formation. This is because the invasion ability can be taken into account to evaluate the protrusion-forming ability.

Embedding of the cell spheroid in a gel can be carried out by a conventional method. For example, a gel in a molten state is injected into a container for cell culture containing the constructed cell spheroid in a sufficient amount so that the entire cell spheroid is immersed, and the container is allowed to stand to cure the gel, thereby making it possible to embed the cell spheroid in the gel. As the gel, a commercially available gel used for a cell culture substrate, which contains the components constituting the extracellular matrix, may also be used.

When a cell spheroid including the cells having protrusion-forming ability is cultured for a sufficient time, protrusions are formed. Cultivation of the cell spheroid can be carried out in the same manner as in the case of plane-culture of the cells belonging to the same species as the cells constituting the cell spheroid. For example, a cell spheroid embedded in a gel can be cultured in a state of being immersed in a liquid medium for cell culture generally used for plane-culture of the cells belonging to the same species as the cells constituting the cell spheroid at a temperature of 25 to 40° C., preferably 28 to 37° C. under an environment in which carbon dioxide and oxygen concentrations are controlled. The carbon dioxide and the oxygen concentrations in the culture environment can be appropriately adjusted in consideration of the species or the like of the cells to be cultured. As the culture environment, for example, it is preferable that the carbon dioxide concentration be controlled within a range of 4 to 6% by volume and the oxygen concentration within a range of 1 to 22% by volume.

After labeling the cell spheroid with a fluorescent substance, it is imaged with the fluorescence emitted from the fluorescent substance using a fluorescence microscope, and image analysis is performed on the obtained fluorescent plane tomographic image, thereby distinguishing the protrusion from other parts of the cell spheroid to determine the protrusion (steps (a) and (b)). Therefore, it is sufficient for the cell spheroid to be fluorescently labeled at least with the cells constituting the protrusion and the cells in the boundary part between the protrusion and the substantially spherical part of the cell spheroid in which no protrusion is formed, though it is preferable that all the cells constituting the cell spheroid be fluorescently stained.

Fluorescent labeling of a cell spheroid for determining protrusion is performed by binding a fluorescent substance to a biomolecule of cells forming protrusions via a substance specifically binding thereto. For example, the cell spheroid may be fluorescently labeled by subjecting the cell spheroid cultured in order for forming protrusions to fluorescent immunostaining using an antibody against biomolecules present in the cells constituting the cell spheroid. Fluorescent immunostaining may be performed by a conventional method.

The biomolecule to be fluorescently labeled to determine the protrusion is not particularly limited as long as it is a biomolecule present in the cells forming the protrusion. In the protrusion-forming ability evaluation method according to the present invention, it is preferable that the cell spheroid be fluorescently labeled by binding a fluorescent substance to a biomolecule constituting the cytoskeleton, such as actin, tubulin or the like, or a biomolecule constituting a cell membrane, such as phospholipid. Since the cytoskeleton and the cell membrane are located at the peripheral part of the cells, the tip part of the protrusion can be more clearly determined by fluorescently labeling these biomolecules. Among others, it is more preferable to fluorescently label the biomolecules constituting the cytoskeleton, and it is even more preferable to fluorescently label actin. The cytoskeleton, especially the actin fiber, extends towards the cell movement direction in the migrating or invading cells. Therefore, by fluorescently labeling the actin, it is also possible to analyze the movement direction of the cells forming the protrusion, that is, the extension direction of the protrusion.

With regard to the cells constituting the cell spheroid, biomolecules constituting the cytoskeleton and biomolecules constituting the cell membrane may be fluorescently labeled in advance. For example, transformed cells obtained by constantly expressing a chimeric protein obtained by fusing an actin with a fluorescent protein such as GFP etc. are used to constitute a cell spheroid, and the cell spheroid is cultured to fluorescently label the actin, thereby it is possible to obtain a cell spheroid in which the protrusion part is fluorescently labeled. In addition, a cell spheroid constituted by transformed cells in which the entire cytoplasm is fluorescently labeled may also be measured using the protrusion-forming ability evaluation method according to the present invention. For example, in the transformed cells in which the fluorescent protein not localized to a specific organelle but present in the whole cytoplasm is constantly expressed, the entire cytoplasm is fluorescently labeled.

In step (a), a fluorescently labeled cell spheroid is imaged with a fluorescence microscope under irradiation of excitation light of the fluorescent substance used for labeling the protrusion, and a plane tomographic image of the fluorescence emitted from the fluorescent substance is acquired. At this time, a plane tomographic image having a resolution capable of identifying individual cells is acquired. As the fluorescence microscope, for example, a confocal laser microscope equipped with a detector such as a photomultiplier tube, a light sheet microscope or the like may be used. By performing image analysis on the plane tomographic image capable of identifying individual cells constituting the protrusion, it is possible to more clearly determine the protrusion from the plane tomographic image compared with the case based on a plane tomographic image with a lower resolution, and also possible to analyze the structure of the protrusion in more detail. For example, information such as the number of the cells forming the respective protrusions and by what cell arrangement the protrusions are formed can also be acquired by the image analysis.

In addition, with regard to the cells for forming the protrusion, it is preferable to also perform the fluorescent labeling of the biomolecules which is useful for analyzing the physiological state and the physiological activity of the cells in addition to the fluorescent labeling for determining the shape of the cells to acquire the plane tomographic images of the respective fluorescence. Specifically, the excitation light of the respective fluorescence is sequentially irradiated to image the plane tomographic images of the respective fluorescence with the same visual field of microscope as the plane tomographic image acquired in step (a). By analyzing the obtained plane tomographic images having a high resolution, it is also possible to analyze the physiological state and the physiological activity of the respective cells constituting the protrusion part. In this manner, in the protrusion-forming ability evaluation method according to the present invention, since the fluorescent plane tomographic images imaged at a resolution capable of identifying individual cells are subjected to the image analysis, the physiological state and the physiological activity of the cells constituting the protrusion part can be analyzed in more detail.

As the examples of the biomolecules to be fluorescently labeled in order to determine the physiological state or physiological activity of the cells, not for determining the shape of the protrusion part, a nucleic acid can be mentioned. By fluorescently labeling the nucleic acid in the cells, mainly the cell nuclei are fluorescently stained. That is, by analyzing the plane tomographic images of the fluorescence emitted from the nucleic acid, it is also possible to determine the shape of the cell nuclei, the number of cell nuclei per cell, and the like, and also possible to determine the approximate cell cycle of the cells. In addition, it is also possible to measure the cell density in the respective local regions of the cell spheroid. For the fluorescence-staining of the nuclei, it may be properly selected from known fluorescent nucleic acid staining agents, such as DAPI (4',6-diamino-2-phenylindole), PI (propidium iodide), Hoechst 33258, Hoechst 33342, 7-AAD (7Amino actinomycin D) and the like, and used. In addition, the image analysis for determining the cell nucleus region from the plane tomographic images of the fluorescence emitted from the nucleic acid can be performed using a known image analysis method such as the method described in Japanese Unexamined Patent Application Publication No. 2011-75278.

In addition, it is also preferable that at the same time when the peripheral part of the cells, such as the cytoskeleton, the cell membrane or the like, is fluorescently labeled, the nucleic acid in the cell nuclei of the living cells and the nucleic acid in the cell nuclei of the dead cells be labeled with different fluorescence. By analyzing the plane tomographic images of the fluorescence emitted from the nucleic acid, it is possible to determine the live/dead state of the cells constituting the cell spheroid. In this case, it is allowable that only the cell nuclei of the living cells are stained, or only the cell nuclei of the dead cells are stained. The fluorescence-staining of the cell nuclei of the living cells and dead cells may be carried out by conventional methods such as the methods using the commercially available live/dead determination reagents (for example, "Nuclear ID green/red cell viability reagent (manufactured by Enzo Life Science, Inc.,)").

Although the number of the plane tomographic images acquired in step (a) may be one per visual field of microscope, it is preferable to acquire two or more plane tomographic images of the fluorescence microscope having different focal positions, and it is particularly preferable to sequentially move the focal position of the cell spheroid from the position where the focal position is the minimum to the position where the focal position is the maximum, at equal intervals, to acquire a series of the plane tomographic images. For example, in the confocal laser microscope, it is possible to acquire a plurality of plane tomographic images having different focal positions by sequentially imaging the plane tomographic images of the cross sections of the cell spheroid orthogonal to the Z-axis direction, while gradually shifting the confocal region toward the height direction (z-axis direction) of the cell spheroid (while relatively moving the objective lens and the cell spheroid in a direction orthogonal to the optical axis).

By superimposing this acquired series of the plane tomographic image groups on each other, a stereoscopic image of the cell spheroid can be constructed. The distance between the focal positions of the respective plane tomographic images at the time of acquiring this series of the plane tomographic images is preferably smaller than the cells constituting the cell spheroid, for example, 0.5 to 5 μm, so that the respective plane tomographic images can be overlapped more smoothly. Construction of the stereoscopic image from the series of the plane tomographic images can be performed by the image construction methods known in the technical field, such as CT (Computed Tomography).

Since the protrusions are formed in various directions of the cell spheroid, one plane tomographic image can only represent a part of the protrusions of the cell spheroid. In contrast, by determining the protrusions based on the constructed stereoscopic image of the cell spheroid, it is possible to determine the protrusions formed toward any direction of the cell spheroid, and more accurately evaluate the protrusion-forming ability of the cells constituting the cell spheroid.

By performing image analysis on the acquired plane tomographic images or the constructed stereoscopic image of the cell spheroid, the protrusions of the cell spheroid can be determined (step (b)). In the present invention, since the protrusions formed on the cell spheroid are determined by image analysis, it is easy to quantify the number, direction and shape of the protrusions. In addition, since the individual cells in the cell spheroid are visualized, it is also possible to perform a detailed analysis with regard to the morphology of the protrusions and the morphology/motility of the cells constituting the protrusions.

The image analysis for determining the protrusion of the cell spheroid may be carried out using the method, for example, described in Japanese Unexamined Patent Application Publication No. 2009-63509.

Specifically, the protrusions of the cell spheroid may be determined from the stereoscopic image by the following method.

First, based on the fluorescent intensity value per pixel (voxel) of the stereoscopic image, a binarization processing is performed using a predetermined threshold value (a threshold value for distinguishing between a region labeled with fluorescence and a region not labeled with fluorescence). An image obtained by reducing the obtained binarized image to such an extent that the entire cell spheroid is contained in one image is used as an image for protrusion analysis. The fluorescently labeled region in the image for protrusion analysis is recognized as a cell spheroid region. In the image for protrusion analysis, the cell spheroid (fluorescently labeled region) is represented as a mass of a substantially spherical body or as a mass in which a protruding structure is formed from the substantially spherical body.

Thereafter, spheres inscribed in the boundary are established one by one in this cell spheroid region. First, an inscribed sphere having the maximum radius among the spheres inscribed in the boundary of the cell spheroid is established. Next, another inscribed sphere having the maximum radius is established in the region excluding the previously established inscribed sphere. By repeating this operation until the radius of the inscribed sphere reaches a predetermined lower limit value, a region of a plurality of the inscribed spheres can be obtained. The cell spheroid region is then divided into a plurality of regions in such a manner that each region includes one inscribed sphere and the points outside the inscribed spheres are respectively included in a region including an inscribed sphere nearest to the point. As a result, all of the points in the cell spheroid region are divided into any one of the regions including the inscribed spheres. Each of these divided "regions including the inscribed spheres" is hereinafter referred to as a "spherical region".

In order to distinguish between the protrusion and the substantially spherical part of the center of the cell spheroid, a threshold value of the diameter of the inscribed spheres is predetermined. The threshold value of the diameter of the inscribed sphere is set so that the spherical region in which the diameter of the inscribed sphere is smaller than the threshold value is distinguished as the protrusion, and the spherical region in which the diameter of the inscribed sphere is larger than the threshold value is distinguished as the substantially spherical part. The threshold value may be set as a specific number of pixels or set by a ratio to the maximum value of the inscribed sphere (for example, "a length (the number of pixels) of ½₀ of the maximum value of the inscribed sphere"). The maximum value of the inscribed sphere is the inscribed sphere which contains the most of the substantially spherical part of the center of the cell spheroid. The spherical region in which the diameter of the inscribed sphere is smaller than the predetermined threshold value is distinguished as the protrusion part, and the spherical region in which the diameter of the inscribed sphere is equal to or larger than the predetermined threshold value is distinguished as the region other than the protrusion part (non-protrusion part).

If there is a spherical region adjacent to three or more spherical regions among the spherical regions constituting the protrusion, it is determined that the protrusion has a branched structure. Among the spherical regions constituting the protrusions, in a spherical region adjacent to N (N is an integer of 3 or more) spherical regions, it branches into N−1 spherical regions. On the other hand, when all the spherical regions constituting the protrusions are in contact with only one or two spherical regions, it is determined that the protrusion part is linear without branching.

The length of the protrusion part can be measured as a distance connecting the center points of the inscribed spheres of each spherical region constituting the protrusion part with a straight line. The length of the protrusion having the branched structure is the maximum value of the distance obtained by connecting with a straight line the center points of the inscribed spheres of the adjacent spherical regions among the protrusions.

The width of the protrusion corresponds to the diameter of the inscribed sphere of the spherical region constituting the protrusion. The maximum width of the protrusion is the maximum value of the diameter of the inscribed sphere of the spherical region constituting the protrusion.

Image analysis for determining the protrusions of the cell spheroids from the plane tomographic image can be performed in the same manner as the image analysis for determining the protrusions of the cell spheroids from the stereoscopic images described above except that inscribed circles are established instead of inscribed spheres.

Based on the determined protrusions, the protrusion-forming ability of the cell spheroid is evaluated (step (c)). The evaluation of the protrusion-forming ability of the cell spheroid may be performed based on, for example, the length and maximum width (thickness) of each protrusion formed on the cell spheroid, or the presence/absence of branching. The length, maximum width and the presence/absence of branching is measured for all of the protrusions determined by the image analysis. Thereafter, based on such information, the number, directionality, maximum length, average length per protrusion, and number of branches per protrusion of the protrusions formed on the cell spheroid can be determined.

The evaluation of the protrusion-forming ability in step (c) is preferably performed based at least on one selected from the group consisting of the number, directionality, maximum length, average length per protrusion, number of branches per protrusion, and average number of branches per protrusion of the protrusions formed on the cell spheroid. The larger the number of protrusions formed on the cell spheroid is, or the longer the maximum length of the protrusions formed on the cell spheroid is, or the larger the average number of branches per protrusion of the protrusions formed on the cell spheroid is, or the larger the average number of branches per protrusion of the protrusions formed on the cell spheroid is, the higher is evaluated the protrusion-forming ability of the cell spheroid.

The evaluation of the protrusion-forming ability in step (c) may also be performed based on the ratio between the total volume of the cell spheroid and the volume of the substantially spherical central part of the cell spheroid ([volume of substantially spherical central part of cell spheroid (voxel)]/[total volume of cell spheroid (voxel)]) (hereinafter, may be referred to as "central sphere volume ratio"). Here, "the substantially spherical central part of the cell spheroid" is equivalent to the aforementioned non-protrusion part. The smaller the central sphere volume ratio is, the larger is the volume of the protrusion part, and the protrusion-forming ability of the cell spheroid is evaluated to be higher. Further, instead of the central sphere volume ratio, the protrusion-forming ability may also be evaluated based on the ratio between the volume of the protrusion part and the volume of the substantially spherical central part of the cell spheroid, or the ratio between the volume of the protrusion part and the total volume of the cell spheroid.

The protrusion-forming ability evaluation method according to the present invention can be performed on the cell spheroid obtained after culturing under a specific environment, thereby making it possible to evaluate the protrusion-forming ability of the cells constituting the cell spheroid under the same environment. For example, an external stimulation is applied to a cell spheroid embedded in a gel, and the cell spheroid is labeled with a fluorescent substance, followed by performing the protrusion-forming ability evaluation method according to the present invention on this fluorescently labeled cell spheroid, thereby making it possible to evaluate the protrusion-forming ability in a state where the cell spheroid is applied with the external stimulation. This external stimulation may be a transient stimulation, or a continuous stimulation during the cultivation period necessary for protrusion formation.

For example, in the case where the external stimulation is a physiologically active substance, the protrusion-forming ability evaluation method according to the present invention is performed on a cell spheroid in which the protrusions are formed after contacting the physiologically active substance and labeled with a fluorescent subject, thereby making it possible to evaluate the protrusion-forming ability in a state where the cells constituting the cell spheroid are stimulated by the physiologically active substance. More specifically, for example, a cell spheroid embedded in a gel is immersed in a culture medium containing a physiologically active substance, or a physiologically active substance is added to the culture medium in which a cell spheroid is immersed, then the cell spheroid is cultured for a sufficient time so that the cell spheroid can be stimulated by the physiologically active substance. Depending on the culture period, the culture medium containing the physiologically active substance may be replaced with a new culture medium not containing the physiologically active substance to continue the cultivation.

The physiologically active substance refers to a substance involved in various biological reaction controls. The physiologically active substance to be used as the external stimulation in the present invention may be a substance originally present in a living body, such as a vitamin. hormone, antibody, etc., and may also be a substance not originally present in a living body, such as an enzyme inhibitor, a chemically synthesized product used for active ingredient of pharmaceutical product, or the like. The physiologically active substance may be any of the proteins, peptides, complex proteins such as glycoproteins, saccharides, polysaccharides, lipids, nucleic acids, and the low-molecular-weight compounds.

In the protrusion-forming ability evaluation method according to the present invention, cell spheroids of three-dimensional structure under an environment similar to that of in vivo cells are used to evaluate the protrusion-forming ability. For this reason, by using the protrusion-forming ability evaluation method according to the present invention to evaluate the medical efficacy of active ingredients of various pharmaceuticals including anticancer agents, it is possible to obtain an evaluation result closer to the medicinal efficacy obtained by administering the medicine to the living body, as compared with the case where the plane-cultured cells are used.

For example, a cell spheroid containing cancer cells collected from a cancer patient is immersed and cultured in a culture medium containing an anticancer agent and the protrusion-forming ability evaluation method according to the present invention is performed, thereby making it possible to evaluate the protrusion-forming ability of the cancer cells of the cancer patient in a state where the cancer cells are treated with the anticancer agent. In the cancer cells in which the Epithelial to Mesenchymal Transition (EMT) is controlled, the protrusion-forming ability decreases or disappears. For this reason, when it is evaluated that the protrusion-forming ability is lower than that of the cancer cells untreated with the anticancer agent, it is evaluated that the EMT of the cancer cells is suppressed by the anticancer agent, that is, the cancer cells of the cancer patient are sensitive to the anticancer agent and anticancer effects can be expected by administering the anticancer agent to the cancer patient.

In the case of stimulating the cell spheroid with an anticancer agent, it is preferable to distinguish between the cell nuclei in living cells and dead cells by fluorescently staining the cell nuclei, in addition to fluorescently labeling the cytoskeleton and the cell membrane in order for determining the shape of the protrusion. The live/dead state of each cell can also be analyzed at the same time by analyzing the plane tomographic image of the fluorescence of the fluorescently labeled cell nuclei in the same microscopic visual field as the plane tomographic image acquired in step (a). If the number of dead cells is apparently increased compared to that before anticancer agent stimulation, it can be evaluated that cell death is induced by the anticancer agent, that is, the cancer cells of the cancer patient are sensitive to the anticancer agent and anticancer effects can be expected by administering the anticancer agent to the cancer patient.

In the case of stimulating the cell spheroid with an anticancer agent, it is possible to fluorescently label the biomolecules considered to be involved in the migration and invasion ability of the cells such as cadherin, proteases such as MMP, or the like, in addition to fluorescently labeling the cytoskeleton and the cell membrane. The expression level and the localization of biomolecules in the cells can be analyzed by analyzing the plane tomographic image of the fluorescence of the fluorescently labeled biomolecules in the same microscopic visual field as the plane tomographic image acquired in step (a). The obtained analysis results can be expected to contribute to the elucidation of the relationship between the cell protrusion formation and cell migration/invasion.

The external stimulation applied to the cell spheroid may be a radiation irradiation. The radiation may be a non-ionizing radiation such as visible light or infrared light, or may be an ionizing radiation such as ultraviolet light, X-ray, or gamma ray. Hereinafter, the stimulation by radiation irradiation is sometimes referred to as "light stimulation".

The light stimulation to the cell spheroid can be performed by radiation irradiation. The light stimulation may be performed by irradiating the entire cell spheroid, or irradiating only a part of the cell spheroid, or by irradiating a part of the gel in which the cell spheroid is embedded rather than the cell spheroid itself. In addition, the cultivation of the cell spheroid in order for protrusion formation can be carried out in such a manner that the cell spheroid is cultured without light stimulation after being applied with the light stimulation, or the radiation is continuously irradiated during the cultivation period. The protrusions formed by culturing the cell spheroid with light stimulation before the cultivation or with continuous light stimulation during the cultivation are used for performing the protrusion-forming ability evaluation method according to the present invention.

In the case of applying a directional stimulation such as the light stimulation, the influence on the cell may vary with the direction of the stimulations even if the strengths of the stimulations (irradiation intensity or illuminance in the case of light stimulation) are the same. Since the protrusion-forming ability evaluation method according to the present invention is performed based on the fluorescence image captured with a resolution capable of identifying individual cells, it is possible to not only evaluate the influence of the wavelength of the irradiated light, the irradiation intensity, and the illuminance on the protrusion-forming ability but also evaluate the influence of the light irradiation direction on the protrusion-forming ability and the cell movement direction.

The external stimulation applied to the cell spheroid may also be a temperature stimulation such as a thermal stimulation or cold stimulation. The thermal stimulation can be applied by raising the culture temperature of the cell spheroid, while the cold stimulation can be applied by lowering the culture temperature of the cell spheroids.

EXAMPLES

Next, the present invention will be described in more detail by showing examples, but the present invention is not limited to the following examples.

Example 1

The protrusion-forming ability of the cell spheroids of the cancer cells treated with various anticancer agents was examined. As the cancer cells, MDA-MB231 cells of a cultured cell strain established from a human breast cancer cells were used. MDA-MB 231 cells were cultured under a condition with a temperature of 37° C. and a $CO_2$ concentration of 5 vol % in a culture medium of DMEM containing 10% FBS.

Five kinds of anticancer agents, L-Sulforaphane (manufactured by Sigma Corporation), Batimastat (manufactured by Sigma Corporation), Mitomycin C (manufactured by Wako), Paclitaxel (manufactured by Wako Corporation), and Staurosporine (manufactured by Wako Corporation) were used as anticancer agents.

<Construction of Cell Spheroid Embedded in gel>

Two thousand MDA-MB 231 cells and 5 µL of 10×Spheroid Formation ECM (manufactured by Trevigen, Inc.) were mixed in a culture medium to prepare a cancer cell solution of which the final amount was adjusted to 50 µL using DMEM (phenol red free), and then 50 µL of the cancer cell solution was injected into one well of the U bottom plate for forming a cell spheroid "Prime Surface (registered trademark) U plate" (manufactured by Sumitomo Bakelite Co., LTD.), followed by culturing the cells for 72 hours to form cell spheroids.

The culture medium was removed from the U bottom plate as much as possible by suction while paying attention not to suck the spheroids, followed by carefully adding 100 µL of Matrigel (manufactured by Corning Incorporated) to the well. The U bottom plate was allowed to stand in an incubator at 37° C. for 1 hour, and the gel was cured to construct a cell spheroid embedded in a gel.

<Anticancer Agent Treatment and Treatment for Live/Dead Determination>

100 µL of culture mediums containing L-Sulforaphane (final concentration: 10 µM), Batimastat (final concentration: 4 µM), Mitomycin C (final concentration: 10 µM), Paclitaxel (final concentration: 4 µM), or Staurosporine (final concentration: 1 µM) was added on the gel in which the cell spheroids were embedded, and then 0.1 µL (1/1000 of the culture medium amount) of "Nuclear ID green/red cell viability reagent" (manufactured by Enzo Life Science, Inc.) was further added thereto, followed by culturing them for 48 hours to infiltrate. By adding the live/dead determination reagent, the living cells were stained with red fluorescence and the dead cells were stained with green fluorescence. As a control, a cultivation in which a culture medium containing only the live/dead determination reagent was used was carried out in the same manner as the above-described cultivation except that the anticancer agents were not added.

<Anticancer Agent Treatment and Actin Staining>

The cell spheroids embedded in the gel were cultured in the culture mediums containing various anticancer agents for 48 hours in the same manner as described in the section <Anticancer agent treatment and Treatment for Live/dead Determination> except that the live/dead determination reagent was not added. Thereafter, only the culture medium was removed by suction while paying attention not to suck the gel, and 150 µL of 4% paraformaldehyde solution was added on the gel, followed by allowing it to stand at room temperature for 30 minutes to fix the cell spheroids. The fixed cell spheroids were washed once with PBS (−), then 150 µL of 0.1% Triton X-100/PBS was added to perform the permeation treatment at room temperature for 1 hour. After the permeation treatment, the cell spheroids were washed once with PBS (−), then Acti-stain 670 (manufactured by Cytoskeleton, Inc.) diluted 100-fold with PBS was added and reacted overnight at 4° C. to perform actin staining.

<Acquisition of Fluorescence Image>

The fluorescently labeled samples prepared in the above-described sections <Anticancer Agent Treatment and Treatment for Live/dead Determination> and <Anticancer Agent Treatment and Actin Staining> were imaged with a confocal laser microscope "FV 1200" (manufactured by Olympus Corporation). A 20-fold objective lens (LUCPLFLN×20) was used to image, and the Z-slice interval was 2 µm. The total number of Z-slices was 60 to 100.

<Construction of Stereoscopic Image>

The series of plane tomographic image groups obtained by imaging the respective fluorescently labeled samples were superimposed to construct a stereoscopic image. The obtained stereoscopic image was binarized to obtain a binarized image.

Figure 2:
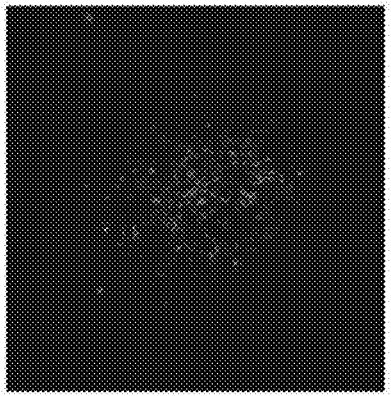
FIG. 2 shows the binarized image of the actin-stained fluorescently labeled sample untreated with the anticancer agent in Example 1.

FIG. 1 shows the binarized images of the anticancer agent-untreated fluorescently labeled sample and the Batimastat-treated fluorescently labeled sample in Example 1, the fluorescently labeled samples being treated with the live/dead determination reagent. In addition, FIG. 2 shows the binarized image of the anticancer agent-treated fluorescently labeled sample in Example 1, the fluorescently labeled sample being stained with actin. In the figures, "Live" represents the fluorescence image of the cell nuclei of the living cells, "Dead" represents the fluorescence image of the cell nuclei of the dead cells, and "Actin" represents the fluorescence image of the actin. "Z-axis" represents the fluorescence image seen from the Z axis direction of the cell spheroid.

<Live/Dead Determination>

For the binarized images obtained from the fluorescently labeled samples treated with the live/dead determination reagent, the number of cell nuclei of red fluorescence and green fluorescent were measured. Quantitative results are shown in Table 1. As a result, the number of dead cells was small in the anticancer agent-untreated sample, whereas the number of dead cells in the Batimastat-treated sample was about 24%, which is larger than that in the anticancer agent-untreated sample, and in the Staurosporine-treated sample, the number of dead cells was about 70%, which is very large. These results indicate that cell death was induced by the anticancer effect of Batimastat and Staurosporine, MDA-MB 231 cells were sensitive to Batimastat and Staurosporine, and the sensitivity against Staurosporine is higher than the sensitivity against Batimastat.

TABLE 1

| Anticancer agent | Control | Batimastat | Staurosporine |
|---|---|---|---|
| Number of Living cells | 3624 ± 504 | 1738 | 576 ± 67 |
| Number of Dead cells | 70 ± 15 | 562 | 1631 ± 414 |

<Determination of Protrusion Part>

An image obtained by reducing the binarized image obtained from the actin-stained fluorescently labeled sample to such an extent that the entire cell spheroid is contained in one image was used as the image for protrusion analysis. In the image for protrusion analysis, the fluorescently labeled region was recognized as the cell spheroid region, and inscribed spheres having the largest radii among the spheres inscribed in the boundary of the cell spheroid region were established in such a manner that they are not overlapped with each other, thereby obtaining a plurality of inscribed spheres. Thereafter, the cell spheroid region was divided into a plurality of regions in such a manner that each region includes one inscribed sphere and the points outside the inscribed spheres were respectively included in a region including an inscribed sphere nearest to the point, thereby setting the spherical regions. A threshold value of the diameter of the inscribed spheres was set to 50 μm, which corresponds to the size of 2 to 3 cells, and the spherical region including an inscribed sphere having a diameter of less than the threshold value was defined as a protrusion part and spherical regions including an inscribed sphere having a diameter of equal to or larger than the threshold value were defined as a region other than the protrusion part (non-protrusion part).

<Evaluation of Protrusion-Forming Ability>

Figure 3:
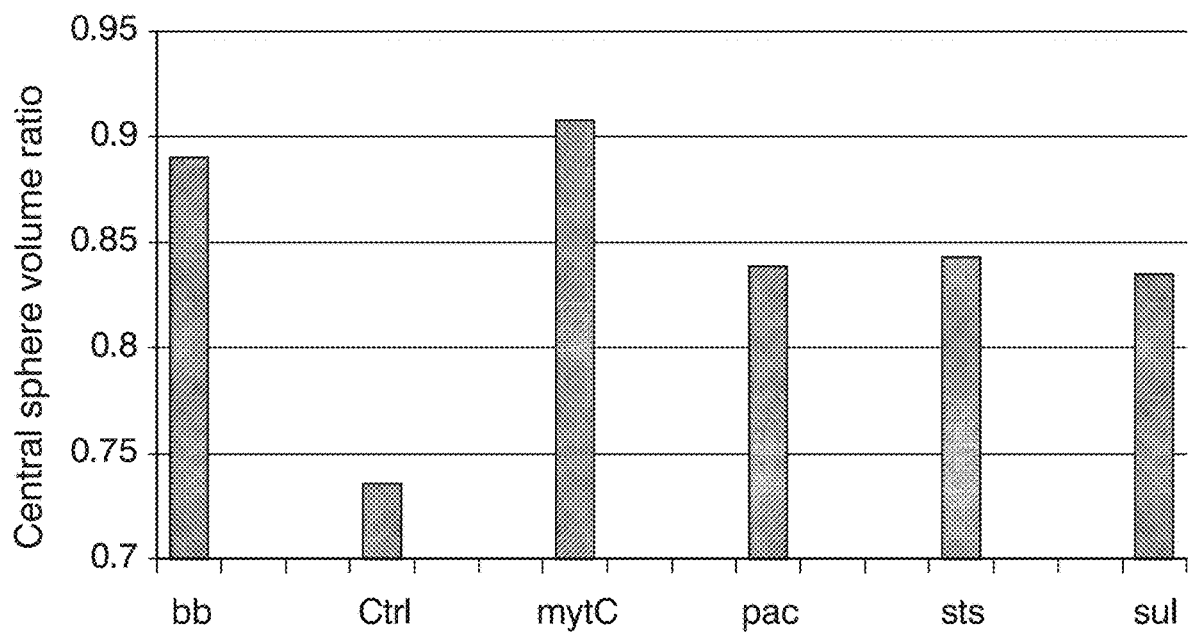
FIG. 3 shows the graph of the results of the central sphere volume ratios ([volume (voxel) of substantially spherical central part of cell spheroid]/total volume of cell spheroid (voxel)]) measured from the stereoscopic images of the cell spheroids treated with the respective anticancer agents in Example 1.

Based on the volumes of the protrusion part and non-protrusion part distinguished in accordance with the manner described above, a central sphere volume ratio was calculated. Specifically, the central sphere volume ratio was calculated by [volume of non-protrusion part (voxel)]/([volume of protrusion part (voxel)]+[volume of non-protrusion part (voxel)]). The calculated results are shown in FIG. 3. In the figure, "Ctrl" represents an anticancer agent-untreated sample, "bb" represents a Batimastat-treated sample, "mytC" represents a Mitomycin C-treated sample, "pac" represents a Paclitaxel-treated sample, "sts" represents a Staurosporine-treated sample, "Sul" represents an L-Sulforaphane-treated sample. As a result, in the anticancer agent-untreated sample, the central sphere volume ratio was small and many protrusions were formed. In contrast, in all of the anticancer agent-treated samples, it was quantitatively found that the central sphere volume ratios were larger than that of the anticancer agent-untreated sample and the numbers of the formed protrusions were smaller than that of the anticancer agent-untreated sample. In particular, the Mitomycin C-treated sample and the Batimastat-treated sample showed a higher central sphere volume ratio as compared with the remaining three anticancer agent-treated samples, and the protrusion formation was suppressed more strongly as compared with the remaining three anticancer agent-treated samples. From these results, it was evaluated that the protrusion-forming ability of MDA-MB 231 cells treated with these five anticancer agents was lowered as compared with when the anticancer agents were not used. In other words, it was found that the protrusion forming-ability of MDA-MB 231 cells reduces by these five anticancer agents, and that MDA-MB 231 cells were sensitive to all of these five anticancer agents and the sensitivities to Mitomycin C and Batimastat were particularly high.

<Evaluation of Protrusion-Forming Ability Based on Plane Tomographic Image>

Figure 4:
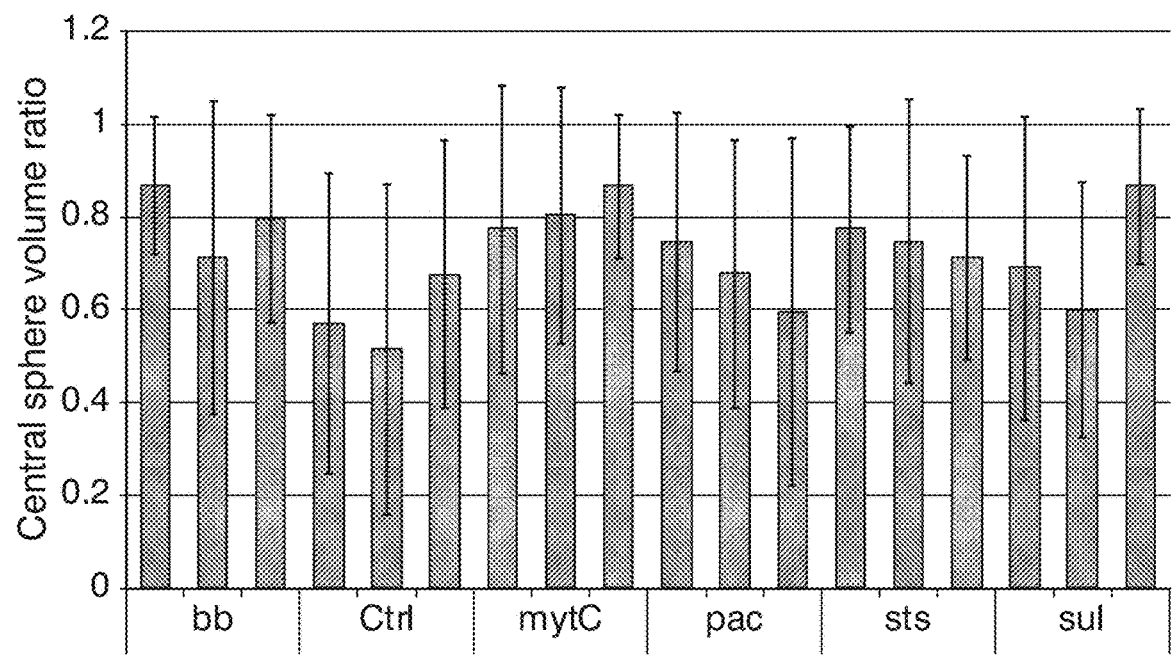
FIG. 4 shows the graph of the results of the central sphere volume ratios ([volume (voxel) of substantially spherical central part of cell spheroid]/total volume of cell spheroid (voxel)]) measured from the plane tomographic images of the cell spheroids treated with the respective anticancer agents in Example 1.

Among the series of the plane tomographic image groups acquired from the actin-stained fluorescently labeled sample, three plane tomographic images of the lower position, the middle position, and the upper position in the Z-axis direction were selected, and the protrusion parts were determined based on the respective plane tomographic images, then the central sphere volume ratios were calculated based on the volumes of the protrusion part and non-protrusion part. The calculated results are shown in FIG. 4. Among the three columns of the respective anticancer agent-treated samples, the column on the left shows the result from the plane tomographic image at the lower position of the cell spheroid, the column on the middle shows the result from the plane tomographic image at the middle position of the cell spheroid, and the column on the right shows the result from the plane tomographic image at the upper position of the cell spheroid. As a result, similarly to the result based on the stereoscopic image, there was a tendency in which the central sphere volume ratios of the anticancer agent-treated samples were larger than that of the anticancer agent-untreated sample, and the numbers of the formed protrusions of the anticancer agent-treated samples were smaller than that of the anticancer agent-untreated sample. However, the variation (standard deviation) of the measured values was large, and the central sphere volume ratios for the cross sections at each position were significantly different from each other, and the difference between the anticancer agent-untreated sample and the anticancer agent-treated samples was also very small. From these results, it is apparent that an evaluation result with a high reliability can be obtained based on a stereoscopic image rather than based on a plane tomographic image.

In the protrusion-forming ability evaluation method according to the present invention, it is possible to profile the mechanism of action (MOA) of the drugs by carrying out the protrusion-forming ability evaluation and the live/dead determination of the cells for the cell spheroids. By practicing the present invention on a compound of which the mechanism of action is unknown, it is possible to estimate the mechanism of action of the compound.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A method for evaluating a protrusion-forming ability of cell spheroids, the method comprising:
   step (a) of imaging a cell spheroid labeled with a fluorescent substance using a fluorescence microscope at a resolution capable of identifying individual cells, and acquiring a plane tomographic image of a fluorescence emitted from the fluorescent substance, step (b) of analyzing the plane tomographic image acquired in step (a) to determine a protrusion part of the cell spheroid, and step (c) of evaluating a protrusion-forming ability of the cell spheroid based on the protrusion part determined in step (b), wherein:

in step (a), two or more plane tomographic images of the fluorescence emitted from the fluorescent substance are acquired, the tomographic images having different focal positions, in step (b), the two or more plane tomographic images acquired in step (a) are superimposed to construct a stereoscopic image of the cell spheroid, and the stereoscopic image is analyzed to determine the protrusion part of the cell spheroid, and in step (c), the protrusion-forming ability of the cell spheroid is evaluated based on one of (i) a ratio between a total volume of the cell spheroid and a volume of a substantially spherical central part of the cell spheroid, (ii) a ratio between a volume of the protrusion and a volume of a substantially spherical central part of the cell spheroid, and (iii) a ratio between a volume of the protrusion and a total volume of the cell spheroid.

2. The method according to claim 1, wherein the cell spheroid to be imaged in step (a) is a cell spheroid in which a cytoskeleton is further fluorescently labeled.

3. The method according to claim 1, wherein:

the cell spheroid to be imaged in step (a) is a cell spheroid in which a nucleic acid is further fluorescently labeled, and in step (a), a plane tomographic image of the fluorescence emitted from the nucleic acid is also acquired.

4. The method according to claim 3, further comprising:

step (d) of analyzing the plane tomographic image of the fluorescence emitted from the nucleic acid of the cell spheroid to determine live/dead of respective cells constituting the cell spheroid.

5. The method according to claim 1, wherein in step (c), the protrusion-forming ability of the cell spheroid is evaluated based on one of a length, a maximum width, and presence/absence of branching of each protrusion formed on the cell spheroid.

6. The method according to claim 1, wherein in step (c), the protrusion-forming ability of the cell spheroid is evaluated based on one or more selected from the group consisting of a number, a directionality, a maximum length, an average length per protrusion, and an average number of branches per protrusion of protrusions formed on the cell spheroid.

7. The method according to claim 1, wherein the cell spheroid is embedded in a gel.

8. The method according to claim 7, wherein:

the cell spheroid a protrusion of which is labeled with the fluorescent substance in step (a) is obtained by applying an external stimulation to the cell spheroid embedded in the gel to form the protrusion, and then labelling the protrusion with the fluorescent substance, and the protrusion-forming ability is evaluated in a state where the cell spheroid is applied with the external stimulation.

9. The method according to claim 8, wherein:

the external stimulation is a physiologically active substance, and the cell spheroid to be imaged in step (a) is a cell spheroid in which a protrusion is formed on the cell spheroid after contacting with the physiologically active substance, and labeled with the fluorescent substance.

10. The method according to claim 9, wherein the physiologically active substance is an anticancer agent.

11. The method according to claim 8, wherein:

the external stimulation is one of a non-ionizing radiation and an ionizing radiation, and the cell spheroid to be imaged in step (a) is a cell spheroid in which the protrusion is formed on the cell spheroid after irradiating at least a part of the cell spheroid embedded in the gel with the one of the non-ionizing radiation and the ionizing radiation, and labeled with the fluorescent substance.

\* \* \* \* \*